United States Patent
Farnè

(10) Patent No.: US 6,802,212 B2
(45) Date of Patent: Oct. 12, 2004

(54) SYSTEM AND METHOD OF PRODUCING TIRES AND ON-LINE TESTING ELECTRICAL CONDUCTIVITY

(75) Inventor: Maurizio Farnè, Aprilia (IT)

(73) Assignee: Bridgestone Corporation, Tokyo (JP)

(*) Notice: Subject to any disclaimer, the term of this patent is extended or adjusted under 35 U.S.C. 154(b) by 0 days.

(21) Appl. No.: 10/128,173

(22) Filed: Apr. 22, 2002

(65) Prior Publication Data
US 2002/0166372 A1 Nov. 14, 2002

(51) Int. Cl.⁷ ............................................. G01M 17/02
(52) U.S. Cl. ........................ 73/146; 156/136; 156/137; 156/349
(58) Field of Search ................................ 73/146, 146.5; 209/509, 517–521; 156/136–137, 349

(56) References Cited

U.S. PATENT DOCUMENTS

| | | | |
|---|---|---|---|
| 4,268,330 A | * | 5/1981 | Komatsu et al. ............ 156/111 |
| 4,504,919 A | * | 3/1985 | Fujii et al. ................... 700/228 |
| 5,304,270 A | * | 4/1994 | Siegenthaler ................ 156/127 |
| 6,536,597 B1 | * | 3/2003 | Farne et al. ................. 209/520 |

* cited by examiner

Primary Examiner—Edward Lefkowitz
Assistant Examiner—Alandra Ellington
(74) Attorney, Agent, or Firm—Michael R. Huber

(57) ABSTRACT

A system for producing tires having a toroidal carcass, a tread and defined internally by two annular beads. The system includes a production line for manufacturing the tires and a control station for measuring the electrical conductivity of each tire. The production line includes a conveyor which transports the tires between successive parts of the system. A pair of gripping bodies engages the bead portion of the tires and moves the tires vertically from a start position to a measuring position. At least one of the gripping bodies being electrically connected to a first terminal of a measuring instrument. A conducting element is electrically connected to a second terminal of the measuring instrument and is moved into contact with the tread of the tires. The measuring instrument measures the electrical conductivity between the tread and the bead portion of the tires.

20 Claims, 1 Drawing Sheet

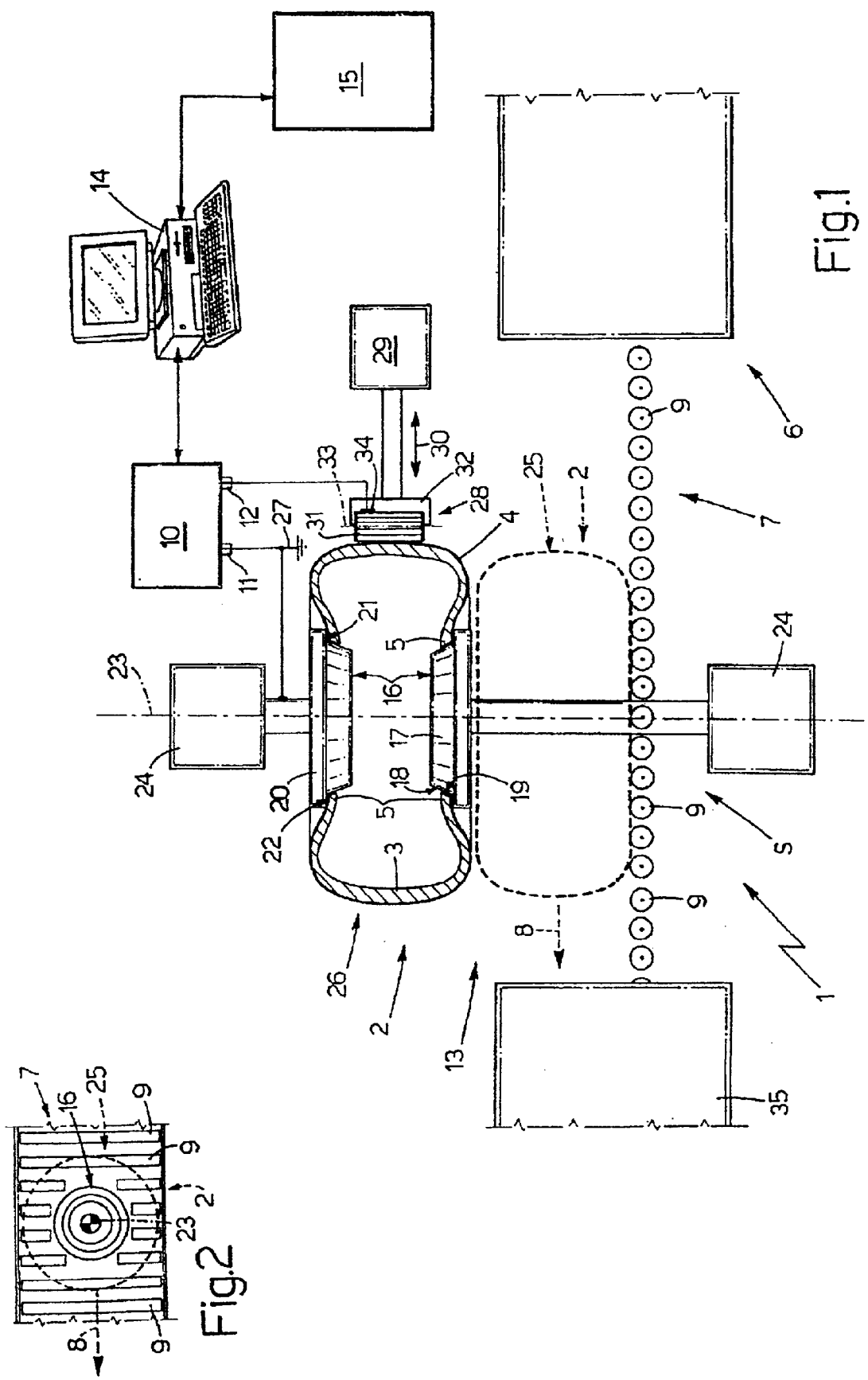

SYSTEM AND METHOD OF PRODUCING TIRES AND ON-LINE TESTING ELECTRICAL CONDUCTIVITY

FIELD OF THE INVENTION

The present invention relates to a system for producing tires.

BACKGROUND OF THE INVENTION

In the road vehicle tire manufacturing industry, forming devices are used to produce green components. These green components are processed and assembled to form green tires, which are then cured in respective molds.

To produce tires according to given specifications, the green components coming off the respective forming devices are normally on-line quality tested to make sure the respective mixes are as required, i.e. are such as to impart the desired physical characteristics to the respective components. And, as it is processed and fed to a tire assembly machine, each component is normally also subjected to various on-line checks, such as: identification checks to identify and make sure the right component is being supplied; quality control to ensure the component has the desired physical characteristics (elasticity, hardness, etc.); dimensional inspection to make sure the shape and size of the component and/or the shape, size and location of part of the component are as required; and structural inspection to ensure the desired distribution of the material (no porosity, etc.) within the component.

Despite all the above checks, however, some tires, even when formed from components individually within the acceptance range, are still found to fall short of the desired characteristics, thus lowering the average quality of the tires produced. Moreover, recent research shows a marked increase in the problem as regards the electrical conductivity of the tires, owing to the tendency to use less carbon black in the manufacture of tires.

SUMMARY OF THE INVENTION

What the art needs is a tire production system designed to eliminate the aforementioned drawbacks, and which, in particular, is cheap and easy to implement.

According to the present invention, there is provided a tire production system for producing tires with a toroidal carcass, a tread and defined internally by two annular beads. The system includes a production line for assembling the tires and a control station located at the end of the production line for taking on-line measurements of the electrical conductivity of each tire.

The present invention also relates to a tire production method for measuring the conductivity of a tire. The tire includes a toroidal carcass having a tread and defined internally by two annular beads. The tire is fed to a control station and placed into a start position. The beads of the tire are engaged by two opposing gripping bodies which move the tire into a measuring position by a combined first movement of the gripping bodies. The control station then makes a conductivity measurement of the tire while the tire is in the measuring position.

BRIEF DESCRIPTION OF THE DRAWINGS

A non-limiting embodiment of the present invention will be described by way of example with reference to the accompanying drawings, in which:

FIG. 1 shows a schematic side view of one embodiment of the system according to the present invention; and FIG. 2 shows a smaller-scale plan view, with parts removed for clarity, of a detail in FIG. 1.

EMBODIMENTS OF THE INVENTION

Number 1 in FIG. 1 indicates as a whole a system for producing tires 2. Each tire 2 includes a toroidal carcass 3 having a tread 4 and defined internally by two annular beads 5. System 1 comprises a known production line 6 for assembling tires 2 from a number of components (not shown) fed onto production line 6.

An end portion of production line 6 has a roller conveyor 7 for feeding the green or cured tires 2 in a horizontal direction 8. Roller conveyor 7 includes a number of horizontal, equally spaced rollers 9. Some of rollers 9 may be powered to feed tires 2 forward, while the others are mounted idly to simply support tires 2. A control station S is located along conveyor 7 to on-line measure the electrical conductivity of each tire 2 between respective tread 4 and at least one respective bead 5.

Control station S comprises an electrical-conductivity measuring instrument 10 having two terminals 11 and 12; and an actuating system 13. Actuating system 13 places terminal 11 electrically in contact with at least one bead 5 of a tire 2 at control station S and places terminal 12 electrically in contact with tread 4 of a tire 2 at control station S.

Measuring instrument 10 provides for measuring the electrical conductivity (or electrical resistance) between its terminals 11 and 12, is of known type (e.g. the measuring instrument marketed by the trade name KEITHELEY 487), and has a relatively wide reading range (preferably 0 ohm to 1 Gohm).

Measuring instrument 10 is connected to a processing unit 14 (preferably an industrial computer) by an IEEE488 interface allowing processing unit 14 to control all the functions of measuring instrument 10. Processing unit 14 is, in turn, connected to a control unit 15 for controlling production line 6 and, among other things, also conveyor 7 and actuating system 13.

Actuating system 13 comprises two gripping bodies 16, each of which provides for engaging a respective bead 5 of a tire 2 at control station S. More specifically, each gripping body 16 is a body of revolution defined by the union of a truncated-cone-shaped portion 17 and a cylindrical portion 20. Truncated-cone-shaped portion 17 has a lateral surface 18 for engaging a base surface 19 of a respective bead 5. Cylindrical portion 20 is coaxial with truncated-cone-shaped portion 17 and has a base surface 21 defining a supporting surface for an outer lateral portion 22 of a respective bead 5.

At control station S, the two gripping bodies 16 are positioned with their respective axes aligned with a vertical axis 23. Gripping bodies 16 are movable along axis 23 by means of respective actuating devices 24, which are controlled by control unit 15, preferably comprise hydraulic linear actuators, and preferably also provide for rotating gripping bodies 16 synchronously about axis 23.

In actual use, conveyor 7 feeds a tire 2 from production line 6 to control station S, and sets tire 2 into a start position 25 (shown by the dash line in FIGS. 1 and 2) in which tire 2 is substantially coaxial with vertical axis 23 and therefore with the two gripping bodies 16. Under the control of actuating devices 24, gripping bodies 16 then engage opposite sides of tire 2 at respective beads 5 to grip tire 2 with a given force; and, having gripped tire 2 in start position 25, gripping bodies 16, again under the control of actuating devices 24, move tire 2 along vertical axis 23 into a measuring position 26 (shown by the continuous line in FIG. 1).

Obviously, if the tire 2 in start position 25 is not perfectly coaxial with gripping bodies 16, the truncated-cone-shaped portions 17 of gripping bodies 16, by being eased first inside beads 5 of tire 2, automatically center tire 2 coaxially with gripping bodies 16.

In the embodiment of FIG. 1, gripping bodies 16 are made entirely of electrically conducting (typically metal) material and are connected electrically to both terminal 11 of measuring instrument 10 and the ground 27 of system 1. In an alternative embodiment, only truncated-cone-shaped portions 17 of gripping bodies 16 are made of electrically conducting material, while cylindrical portions 20 of gripping bodies 16 are made of electrically insulating material.

As shown in FIG. 2, at control station S, some of rollers 9 of conveyor 7 are shorter than the other rollers 9 to allow the bottom gripping body 16 to pass through the surface defined by rollers 9.

Actuating system 13 also comprises a conducting element 28 connected electrically to terminal 12 of measuring instrument 10 and insulated electrically from ground 27 of system 1; and an actuating device 29 for moving conducting element 28, in a horizontal direction 30 perpendicular to vertical axis 23, into contact with tread 4 of a tire 2 in the measuring position 26 at control station S.

Conducting element 28 is defined by a cylinder 31 fitted to a support 32 integral with actuating device 29, so as to rotate idly about a respective central vertical axis 33 parallel to vertical axis 23. Cylinder 31 is insulated electrically from support 32 so as to be insulated electrically from ground 27 of system 1, and is connected electrically to terminal 12 by a respective sliding contact 34.

Preferably, the size of conducting element 28 and the force with which actuating device 29 holds conducting element 28 in contact with tread 4 are such as to produce, between conducting element 28 and tread 4, a contact surface substantially similar to the typical contact surface between tread 4 and the road surface.

Operation of control station S will now be described with reference to a tire 2 fed by conveyor 7 into start position 25 at the control station.

Once tire 2 is fed into start position 25 (detected by known optical sensors not shown), conveyor 7 is arrested locally to keep tire 2 in start position 25; and, at the same time, gripping bodies 16 are activated to grip tire 2 by respective beads 5, as described previously, and move tire 2 into measuring position 26.

Once tire 2 is set to measuring position 26, conducting element 28 is moved by actuating device 29 into contact with respective tread 4 with a given contact force; at which point, processing unit 14 activates measuring instrument 10 to determine the electrical conductivity (or electrical resistance) between terminals 11 and 12, i.e. between tread 4—or rather the portion of tread 4 in contact with conducting element 28—and beads 5.

When measuring the electrical conductivity (or electrical resistance) between terminals 11 and 12, tire 2 may be rotated about axis 23 by the two actuating devices 24, so that the mean electrical conductivity value measured between terminals 11 and 12 reflects the mean electrical conductivity value between beads 5 and a central strip of tread 4 of a whole, thus increasing the significance and accuracy of the electrical conductivity measurement.

On receiving the electrical conductivity (or electrical resistance) measurement of tire 2 from measuring instrument 10, processing unit 14 memorizes the measurement in a database for subsequent statistical processing, and compares the measurement with a reference value (or range) to determine acceptance or not of tire 2. Depending on the outcome of the comparison (or several successive comparisons), processing unit 14 transmits to control unit 15 a command to accept or reject tire 2, to arrest processing and request operator assistance, or to change the processing parameters on production line 6.

Once the measurement is completed, conducting element 28 is detached from tread 4 of tire 2, and tire 2 is restored to start position 25 by a further combined movement of gripping bodies 16 by actuating devices 24. Once restored to the start position 25, tire 2 is released by gripping bodies 16 and fed by conveyor 7 to successive parts 35 of system 1 for further processing (e.g. curing) or storage.

At this point, another tire 2 is fed by conveyor 7 into start position 25 at the control station, and the above sequence of operations is repeated.

In an alternative embodiment not shown, once the measurement is completed, tire 2 in the measuring position 26 is moved into an end position (not shown), different from start position 25, by a further combined movement of gripping bodies 16.

In an embodiment not shown, control station S is integrated in a so-called "TUO machine", which provides for finish-testing (in particular, X-raying) finished tires 2 ready for sale. This embodiment is preferable by enabling many parts to be shared between control station S and the "TUO machine", thus reducing the cost of installing control station S.

Control station S at the end of production line 6 enables fast, effective measurement of the electrical conductivity of all the tires 2 coming off production line 6. And, depending on the outcome of the conductivity measurements, any tires 2 not conforming to given specifications are rejected and/or the processing parameters on production line 6 are changed to eliminate the causes. Control station S thus provides for greatly improving the overall average quality of tires 2 produced on line 6.

Moreover, at control station S, the electrical conductivity of each tire 2 is measured, not between any two points of tire 2, but by almost perfectly simulating the actual working conditions of tire 2. In actual use, in fact, the electrical conductivity of tire 2 serves to ground, i.e. discharge to the road, the static electricity accumulated by the vehicle, which is discharged from the vehicle to tire 2 through the metal rim fitted to the respective metal hub of the vehicle and supporting tire 2 at beads 5, and is discharged from tire 2 to the road via the portion of tread 4 contacting the road surface. Similarly, at control station S, the electrical conductivity of tire 2 is measured between beads 5, engaged by gripping bodies 16 structurally very similar to a rim, and a portion of tread 4 of the same size as the portion of tread 4 actually contacting the road surface in use.

What is claimed is:

1. A system (1) for producing tires (2) with a toroidal carcass (3), a tread (4) and defined internally by two annular beads (5), said system (1) comprising:
   a production line (6) for assembling the tires (2);
   a control station (S) located at the end of said production line (6) for on-line measuring the electrical conductivity of each said tire (2);
   said control station (S) comprising an electrical-conductivity measuring instrument (10) having two terminals (11, 12); and actuating means (13) for placing a first said terminal (11) in electrical contact with at least one bead (5) of a tire (2), and for placing a second said terminal (12) in electrical contact with a around engaging portion of tread (4) of said tire (2).

2. A system as claimed in claim 1, wherein said actuating means (13) provide for rotating a said tire (2) at the control station (S) about a central axis of the tire.

3. A system as claimed in claim 1, wherein said first terminal (11) is connected to a ground (27) of the system (1), and said second terminal (12) is insulated with respect to the ground (27) of the system (1).

4. A system as claimed in claim 1, and comprising a processing unit (14) for comparing the result of each said conductivity measurement with at least one reference value, to determine the acceptability of the respective said tire (2).

5. A system as claimed in claim 1, wherein said actuating means (13) comprise a conducting element (28) connected electrically to said second terminal (12); and a second actuating device (29) for moving said conducting element (28) into contact with the tread (4) of a said tire (2) at the control station (S).

6. A system as claimed in claim 5, wherein said second actuating device (29) moves said conducting element (28) into contact with the tread (4) of a said tire (2) in said measuring position (26).

7. A system as claimed in claim 5, wherein said conducting element (28) comprises a cylinder (31) mounted to rotate idly about a respective central axis; said cylinder (31) being connected electrically to said second terminal (12) by a respective sliding contact (34).

8. A system as claimed in claim 1, wherein said actuating means (13) comprise at least one conductive gripping body (16) connected electrically to said first terminal (11); and at least one first actuating device (24) for causing the gripping body (16) to engage a respective bead (5) of a said tire (2) at the control station (S).

9. A system as claimed in claim 8, wherein said actuating means (13) comprise two conductive gripping bodies (16), at least one of which is connected electrically to said first terminal (11); and two first actuating devices (24) for causing the two gripping bodies (16) to engage, on opposite sides, the beads (5) of said tire (2) at the control station (S).

10. A system as claimed in claim 9, wherein said two first actuating devices (24) provide for rotating the two conductive gripping bodies (16) about a common central axis (23).

11. A system as claimed in claim 9, wherein each said conductive gripping body (16) comprises a respective truncated-cone-shaped portion (17) having a lateral surface (18) for engaging a bottom surface (19) of a respective said bead (5).

12. A system as claimed in claim 11, wherein said truncated-cone-shaped portion (17) of each said gripping body (16) is made of electrically conducting material.

13. A system as claimed in claim 11, wherein each said gripping body (16) comprises a respective cylindrical portion (20), which is connected coaxially to the corresponding said truncated-cone-shaped portion (17) so that a base (21) of the cylindrical portion defines a supporting surface for an outer lateral portion (22) of a respective said bead (5).

14. A system as claimed in claim 13, wherein said cylindrical portion (20) of each said gripping body (16) is made of electrically conducting material.

15. A system as claimed in claim 13, wherein said cylindrical portion (20) of each said gripping body (16) is made of electrically insulating material.

16. A system as claimed in claim 9, wherein said production line (6) comprises a horizontal conveyor (7) for setting a said tire (2) into a start position (25) at said control station (S); said two conductive gripping bodies (16), under the control of said first actuating devices (24), engaging said tire (2) in said start position (25) at the control station (S) to impart a first movement to the tire (2) to set the tire (2) into a measuring position (26).

17. A system as claimed in claim 16, wherein said horizontal conveyor (7) comprises a succession of rollers (9) for supporting said tires (2), and at least some of which are powered.

18. A system as claimed in claim 16, wherein said two gripping bodies (16), under the control of said first actuating devices (24), provide for imparting to the tire (2) in said measuring position (26) a second movement, opposite to said first movement, to restore the tire (2) to said start position (25).

19. A system as claimed in claim 18, wherein said movements are effected in a direction (23) perpendicular to a traveling direction (8) of said horizontal conveyor (7).

20. A system as claimed in claim 19, wherein said movements are effected in a vertical direction (23).

* * * * *